United States Patent [19]

Merk et al.

[11] 4,390,732
[45] Jun. 28, 1983

[54] PROCESS FOR THE PRODUCTION OF GUAIACOL GLYCERINE ETHER

[75] Inventors: Wolfgang Merk, Hanau; Rüdolf M. Wagner, Illertissen; Peter Werle, Geinhausen; Robert S. Nygren, Hanau, all of Fed. Rep. of Germany

[73] Assignee: Degussa AG, Frankfurt, Fed. Rep. of Germany

[21] Appl. No.: 347,482

[22] Filed: Feb. 10, 1982

[30] Foreign Application Priority Data

Feb. 25, 1981 [DE]  Fed. Rep. of Germany ....... 3106995

[51] Int. Cl.³ ............................................ C07C 41/03
[52] U.S. Cl. .................................................. 568/648
[58] Field of Search ....................... 568/648, 618, 621

[56] References Cited

U.S. PATENT DOCUMENTS 2,967,892  1/1961  Smith .............................. 568/648 X
3,917,717  10/1975  Griscom ............................. 568/648

FOREIGN PATENT DOCUMENTS 628497  8/1949  United Kingdom ................ 568/648

*Primary Examiner*—Bernard Helfin
*Attorney, Agent, or Firm*—Cushman, Darby & Cushman

[57] ABSTRACT

Guaiacol glycerine ether is obtained in very good yield and in very high purity by reacting glycidol with o-methyoxyphenol in the presence of an alkali hydroxide, an alkali alcoholate, an alkali cyanate or an alkali thiocyanate at 80° to 150° C. An especially effective purification of the crude product can be obtained by adding hydrogen peroxide, preferably prior to cooling.

20 Claims, No Drawings

PROCESS FOR THE PRODUCTION OF GUAIACOL GLYCERINE ETHER

BACKGROUND OF THE INVENTION

Guaiacol glycerine ether for a long time has been used as a means for medicinal lobotomy, see Rompp; Chemie-Lexikon, 5th edition, Volume II.

It is produced, e.g. by reaction of guaiacol with epichlorohydrin in the presence of molar amounts of sodium hydroxide in water (Yakugaku Zasshi 87(8), 967 (1967)). This reaction, however, requires relatively long reaction times at a temperature of around 85°–90° C. and only results in small yields (32%) of guaiacol glycerine ether.

Furthermore, there is described the reaction with glycerine-α-monochlorohydrin. Thereby it is likewise possible to start from epichlorohydrin and to hydrolyze this in a precusor reaction to glycerine-α-monochlorohydrin by addition of a suitable aqueous acid (e.g. 0.2% $H_2SO_4$) (Polish patent No. 48485 (1964)). It is also necessary in the reaction with glycerine-α-monochlorohydrin to use molar amounts of an alkaline catalyst such as sodium hydroxide. The reaction is principally carried out in water, i.e. aqueous alkali or aqueous methanol (Spanish patent No. 212920 (1954), Czech patent No. 107107 (1963), Polish patent No. 42379 (1959)). Of course there has also been described the addition of toluene/butanol mixtures (German OS No. 2256506 (1973)).

All of these processes, if they are carried out at room temperature, proceed only very slowly while on the other hand, at the temperature of the boiling point of the solvent there must be dealt with the considerable formation of color. Furthermore, per 100 kg of guaiacol there is formed about 30 kg of sodium chloride which must be separated from the reaction solution by suitable procedures, to avoid loss of yield it must be washed, and disposed of. Furthermore the process is characterized by a considerable energy cost since solvents having high vaporization enthalpies are distilled.

Besides it is also known to employ 2,3-epoxypropanol, i.e. glycidol, for the reaction with phenols, among others, p-methoxyphenol, see British Pat. No. 628497; tertiary amine or quaternary ammonium salts function as catalysts.

This reaction with glycidol in place of glycerine-α-monochlorohydrin has the great advantage that it can be operated free from solvent and no sodium chloride is obtained. Through this there is eliminated the separation of the sodium chloride and besides the product is free from chlorine.

The disadvantage of this reaction according to the data of the mentioned British Patent is first of all in the yield, which is not very high; employing the mentioned p-methoxyphenol, it is only 50–65% as crude product.

Besides, in applying this reaction to o-methoxyphenol, i.e. guaiacol, the product obtained only has a very low purity. It still contains a considerable portion of the unreacted guaiacol as well as polymeric impurities, besides residue of the catalyst. Also the product is colored.

The purity of the product can be improved by repeated distillation but in addition to the industrial expense the yield naturally goes down still more by such procedure.

The goal of the invention was to develop a process for the production of guaiacol glycerine ether in which the product is obtained in good yield and purity.

SUMMARY OF THE INVENTION

It has now been found that guaiacol glycerine ether can be produced in very good yield and purity in the reaction of glycidol and a methoxyphenol without the presence of a solvent but in the present of a catalyst at a temperature of 80° to 150° C. if the reaction of glycidol with o-methoxyphenol (guaiacol) is carried out and as a catalyst for the reaction there is employed an alkali metal hydroxide, an alkali metal alcoholate, an alkali metal cyanate and/or an alkali metal thiocyanate.

The catalysts mentioned are used in an amount of 0.0003 to 0.1 mole per mole of guaiacol. Preferred are amounts of 0.003 to 0.05 mole per mole of guaiacol.

As alkali metals there are included lithium, sodium, and potassium, Especially suitable catalysts are sodium hydroxide and/or potassium cyanate. The catalysts are best employed in their commercial form. As alkali alcoholates there are suited above all sodium methylate, potassium methylate, sodium ethylate, or potassium ethylate.

Additional suitable catalysts include potassium hydroxide, lithium hydroxide, lithium methylate, lithium ethylate, sodium propylate, potassium propylate, sodium isopropylate, lithium cyanate, sodium cyanate, potassium thiocyanate, sodium thiocyanate, and lithium thiocyanate.

If the catalyst is present in solid form it can be used in fine powder form.

The preferred reaction temperature is 90°–100° C.

Although the sequence of adding reactants is immaterial it has proven favorable to first melt the guaiacol and to add the glycidol to the molten catalyst-containing guaiacol. The formation of ether is accelerated by this procedure. An additional post reaction time is recommended.

The reactants can be employed in equivalent amounts although a slight excess of glycidol, i.e. up to 10 mole %, is preferred.

The crude product whose guaiacol content inter alia is below 0.5 weight %, is subjected to a distillation, best in a film evaporator, e.g. a thin layer evaporator. Before the distillation the alkaline catalyst employed is inactivated with acid. The type of acid, whether inorganic or organic, is immaterial, likewise, the strength of the acid. It is only important that the acids are stable in the temperature range of the reaction and are not volatile or decomposable. Very suitable is the use of lower aliphatic carboxylic acids such as formic acid, acetic acid, and propionic acid.

The acids are employed in equivalent amounts based on the alkaline catalyst.

The guaiacol ether obtained after the distillation is colorless. If desired, it can be subjected to a recrystallization in known solvents for this purpose, as e.g. methyl acetate, ethyl acetate, and propyl acetate or alcohols such as methanol or ethanol. The guaiacol contents, which after the distillation amounts to about 0.3 weight %, after the recrystallization is reduced to practically zero.

Steam distillation is not recommended for the purification of guaiacol glycerine ether.

It has furthermore been found that a particularly effective purification of the crude product occurs if there is introduced into the melt of guaiacol glycerine ether present after the reaction, preferably without any cooling, 0.05 to 0.1 mole of hydrogen peroxide (100 weight %) as an aqueous solution per mole of guaiacol employed. The hydrogen peroxide can be used in commercial concentrations, preferably as 30-70 weight % solution.

Apparently the color-forming materials are destroyed by the addition of the hydrogen peroxide.

The subsequent crystallization of the guaiacol glycerine ether in presence of the above mentioned solvents (in known manner) is made easier thereby.

In using of e.g. ethyl acetate, the melt is cooled below the boiling point of the solvent to about 70° C. and thereupon there is added one to one and a half times the weight of ethyl acetate based on the amount of melt.

The crystallized guaiacol glycerine ether is practically free of guaiacol.

The yield can be still further increased by working up the mother liquor. For this purpose, the solvent is distilled off, e.g. over a thin layer evaporator, and further crude product recovered from the residue, which through distillation and crystallization, as described above, can be converted into pure product.

The advantage of the process of the invention is in the greatly increased yield and the very high purity of the product which far exceeds the pharmacopeia specifications. The free guaiacol content of the pure product is far below 0.03 weight %, in part even below 0.01 weight %, see Example 5; this content was determined by gas chromatography. Likewise the Hazen color number is very low.

Unless otherwise indicated all parts and percentages are by weight.

The process can comprise, consist essentially of, or consist of the stated steps with the recited materials.

The invention is further explained in connection with the following examples.

DETAILED DESCRIPTION

EXAMPLE 1

Guaiacol was heated with stirring to 90° C. in a flask, 0.01 mole of powdered NaOH added and in the course of 2 hours 151.7 grams (2.05 moles) of glycidol dropped in while holding the temperature constant. The homogeneous, yellowish solution was held at the stated temperature for a further 2 hours and treated with 0.01 mole of acetic acid. The gas chromatogrpahic analysis showed 372 grams (93.8% of theory) of guaiacol glycerine ether as well as a residual content of 0.4 weight % of free guaiacol.

EXAMPLE 2

The procedure of Example 1 was employed but there was employed as catalyst 0.006 mole of powdered KOCN. Yield: 373 grams (94.2% of theory) guaiacol glycerine ether, as well as a residual content of 0.2 weight % free guaiacol.

EXAMPLE 3

The procedure was as in Example 2 but there were added 155.4 grams (2.10 moles) of glycidol. Yield: 186.3 grams (94.1% of theory), residual content of guaiacol 0.03 weight %.

EXAMPLE 4

Working Up By Distillation

The formulations of Examples 1 and 2 can be worked up as follows:

1000 grams of the warm reaction melt was distilled over a thin layer evaporator at 200° C./1 mbar. The yield of completely colorless guaiacol glycerine ether was 854 grams(87% of theory).

EXAMPLE 5

Working Up By Treating The Melt

The melt present after the reaction according to Example 1, 2, or 3 was worked up as follows. There were dropped into the warm melt at about 80° C. 10 ml of 30 weight % $H_2O_2$ (0.09 mole of 100% $H_2O_2$) and the mixture stirred for about 10 minutes. After reaching 72°-70° C. there were subsequently added 500 ml of ethyl acetate and the mixture allowed to cool with stirring for about 10 hours. The crystals which precipitated were filtered with suction, washed and dried. Yield: 324 grams (82% of theory). Content of free guaiacol <0.01 weight %. The Hazen color number is about 10.

After distillation of the ethyl acetate there were recovered further amounts of guaiacol glycerine ether either by allowing to stand for a long time or by distillation. The yield thereby increases about 25 grams to about 88% of theory.

What is claimed is:

1. A process for the production of guaiacol glycerine ether comprising reacting o-methoxyphenol with glycidol in the presence of a catalyst selected from the group consisting of alkali metal hydroxides, alkali metal alcoholates, alkali metal cyanates, alkali metal thiocyanates and mixture thereof.

2. A process according to claim 1 carried out in the absence of a solvent.

3. A process according to claim 1 wherein the catalyst is employed in an amount of 0.0003 to 0.05 mole per mole of guaiacol.

4. A process according to claim 3 carried out in the absence of solvent.

5. A process according to claim 3 wherein the catalyst is employed in an amount of 0.0003 to 0.1 mole per mole of guaiacol.

6. A process according to claim 5 wherein there is used as the catalyst sodium hydroxide in powdered form.

7. A process according to claim 3 wherein there is used as the catalyst sodium hydroxide in powdered form.

8. A process according to claim 1 wherein there is used as the catalyst sodium hydroxide in powdered form.

9. A process according to claim 5 wherein there is used as the catalyst potassium cyanate in powdered form.

10. A process according to claim 3 wherein there is used as the catalyst potassium cyanate in powdered form.

11. A process according to claim 1 wherein there is used as the catalyst potassium cyanate in powdered form.

12. A process according to claim 3 carried out in the absence of a solvent and including the step of adding aqueous hydrogen peroxide in an amount of 0.05 to 0.1 mole (calculated as 100 weight % $H_2O_2$) per mole of guaiacol employed to the melt obtained after the reaction at the temperature present at the end of the reaction, subsequently adding a solvent for the guaiacol glycerine ether and crystallizing the guaiacol glycerine ether from said solvent.

13. A process according to claim 7 carried out in the absence of a solvent and including the step of adding aqueous hydrogen peroxide in an amount of 0.05 to 0.1 mole (calculated as 100 weight % $H_2O_2$) per mole of guaiacol employed to the melt obtained after the reaction at the temperature present at the end of the reaction, subsequently adding a solvent for the guaiacol glycerine ether and crystallizing the guaiacol glycerine ether from said solvent.

14. A process according to claim 10 carried out in the absence of a solvent and including the step of adding aqueous hydrogen peroxide in an amount of 0.05 to 0.1 mole (calculated as 100 weight % $H_2O_2$) per mole of guaiacol employed to the melt obtained after the reaction at the temperature present at the end of the reaction, subsequently adding a solvent for the guaiacol glycerine ether and crystallizing the guaiacol glycerine ether from said solvent.

15. A process according to claim 1 carried out in the absence of a solvent and including the step of adding aqueous hydrogen peroxide in an amount of 0.05 to 0.1 mole (calculated as 100 weight % $H_2O_2$) per mole of guaiacol employed to the melt obtained after the reaction at the temperature present at the end of the reaction, subsequently adding a solvent for the guaiacol glycerine ether and crystallizing the guaiacol glycerine ether from said solvent.

16. A process according to claim 12 wherein the aqueous hydrogen peroxide contains 30–70 weight % hydrogen peroxide.

17. A process according to claim 3 wherein there is added 0.05 to 0.1 mole of aqueous hydrogen peroxide (calculated as 100 weight % $H_2O_2$) per mole of guaiacol after the reaction to destroy color-forming impurities.

18. A process according to claim 1 wherein there is added 0.05 to 0.1 mole of aqueous hydrogen peroxide (calculated as 100 weight % $H_2O_2$) per mole of guaiacol after the reaction to destroy color-forming impurities.

19. A process according to claim 1 wherein there is added aqueous hydrogen peroxide after the reaction in an amount sufficient to destroy color-forming impurities.

20. A process according to claim 2 comprising introducing glycidol into molten catalyst containing guaiacol so that glycidol is instantaneously reacted to guaiacol glycerine ether.

* * * * *